United States Patent [19]

Brown

[11] Patent Number: 4,696,816
[45] Date of Patent: Sep. 29, 1987

[54] METHOD FOR TREATING INTERVERTEBRAL DISC DISPLACEMENT WITH ENZYMES

[76] Inventor: Mark D. Brown, 8900 SW. 96 St., Miami, Fla. 33176

[21] Appl. No.: 796,302

[22] Filed: Nov. 7, 1985

[51] Int. Cl.⁴ .............................................. A61K 37/48
[52] U.S. Cl. ..................................................... 424/94
[58] Field of Search ......................................... 424/94

[56] References Cited

U.S. PATENT DOCUMENTS 3,678,158  7/1972  Sussman ................................. 424/94
4,438,108  3/1984  Sanders et al. ........................ 514/56
4,522,814  6/1985  Nonomara et al. .................... 514/54

FOREIGN PATENT DOCUMENTS 2912660  3/1978  Fed. Rep. of Germany ........ 424/94

OTHER PUBLICATIONS

Chem. Abst. 93: 199801k, 1980.
Chem. Abst. 68: 84538w, 1968.
Chem. Abst. 68: 84511g, 1968.

*Primary Examiner*—J. R. Brown
*Assistant Examiner*—John W. Rollins
*Attorney, Agent, or Firm*—Roland Plottel

[57] ABSTRACT

The method for treating intervertebral disc displacement in mammals which comprises injecting into the intervertebral disc space effective amounts of a pharmacologically suitable solution of the enzyme chondroitinase to bring about the selective chemonucleolysis of the nucleus pulposus.

5 Claims, No Drawings

METHOD FOR TREATING INTERVERTEBRAL DISC DISPLACEMENT WITH ENZYMES

BACKGROUND OF THE INVENTION

Disc degeneration and disc herniation are widely occuring conditions which afflict mankind and which cause disabling back and extremity pain. Intradiscal therapy for proved disc displacement is a dramatic breakthrough in the treatment of this common disorder resulting in shorter and less costly hospitalization than cases where surgical intervention is required.

In 1963, Smith, Garvin and Jennings described the pharmacology of an enzyme that would dissolve the herniated disc that causes leg pain by compressing spinal nerves. That enzyme was chymopapain, a material derived from the fruit of the papaya plant. Over a period of twenty years, chymopapain wended its way through the complex four phases of testing prescribed by the Food and Drug Administration and over 40,000 patients have been treated by chemonucleolysis with chymopapain. The approval process was more difficult than normal due to criticism and controversies among the researchers. In 1982, the FDA approved for commercial release Smith Laboratories' Chymodiactin and Travenol's Discase brands of chymopapain.

A 1977 study by Watts of 13,700 patients injected with chymopapain showed an approximately 3% complications rate, including anaphylactic response, neurotoxicity, cardiovascular and other complications resulting in eight deaths. Nevertheless, careful analysis of these data leads to the conclusion that enzyme injection is at least five times safer than laminectomy for patients who do not show improvement after at least two months of conservative treatment and at least two weeks of bedrest, the population for which some form of intervention is indicated.

The concerns about sensitivity reactions to chymopapain led to a search for alternative chemical materials which would act in the same or similar manner on the nucleus pulposus, thereby relieving sciatic pain and other symptoms. Sussman described such a material, collagenase, in his U.S. Pat. No. 3,678,158 issued July 18, 1972. His research showed higher dissolution effect without systemic sensitivity reaction in any of the patients. While collagenase appears to have a good margin of safety at the effective dosage rates and a comparable or reduced complications rate, when compared with chymopapain, post-injection pain, both local and referred, apear$ more severe with collagenase than with chymopapain, suggesting that the ideal enzyme for chemonucleolysis is still to be identified. The present invention identifies a class of cartilage-dissolving enzymes of bacterial origin which appear to be less allergenic and less neurotoxic than chymopapain and at the same time will not disturb the stabilizing collagen components of disc materials.

An advantage of chondroitinase is that it removes the swelling capacity of the disc, which then shrinks, without interfering with the structural portion of the disc. In contrast, chymopapain has a proteolytic activity which may be responsible for its neurotoxicity; while collagenase dissolves the structural portion of the disc, it promotes tissue swelling which may be responsible for post injection pain nerve compression.

It is anticipated chondroitinase will be non-allergenic, as compared to chymopapain, because it is unlikely that a relatively high percentage of the population will be presensitized to it as is the case with chymopapain. Chymopapain is a plant protein that is phylogenetically more remote from mammals than chondroitenases which are of bacterial origin.

SUMMARY OF THE INVENTION

The present invention comprehends the method of treating disc displacement by the use of the enzyme Chondroitinase ABC or the enzyme Chondroitinase AC which have been previously isolated, purified and sold by Seikagaku Kogyo of Tokyo, Japan. Chondroitinase ABC is produced from *P. vulgaris* and Chondroitinase AC is produced from *A. aurescens*. These enzymes are the first cartilage-dissolving materials of bacterial origin to be used for this purpose. The matrix of the nucleus pulposus contains proteoglycans and randomly dispersed collagen fibers. Chymopapain splits the protein core of the acid-aminoglycan molecules, whereas collagenase depolymerizes native collagen. The chondroitinases work by degrading the polysaccharide side chains of the protein polysaccharide complex rather than the protein core. This method of action is of importance because one would anticipate that they would not have the deleterious proteolytic activity associated with chymopapain and collagenase. Chondroitinase AC works on the end of the polysaccharide polymer to cleave easily diffusable dissacharide units while Chondroitinase ABC works to cleave polysaccharides near their attachment to the protein core. Both enzymes function well within the range of normal tissue acid ion concentration.

The present invention further provides novel methods of intradiscal therapy for proved disc displacement utilizing enzymes which incorporate the best features of both chymopapain and collagenase without, as is now believed, the adverse side effects of either of these drugs.

The present invention also provides novel methods for treating low back pain and sciatica in patients who have previously been treated successfully with injections of chymopapain and/or collagenase by making available additional antigenically different intradiscal chemonucleolytic agents which avoid prior sensitization and danger of systemic reaction.

More particularly, it is the object of this invention to provide new improved non-surgical, non-radical methods for the treatment of disc displacement which represent a significant advance in the art.

These and other objects and advantages of this invention will be apparent from the more detailed description which follows.

DESCRIPTION OF THE PREFERRED EMBODIMENTS

Highly purified Chondroitinase AC and ABC, as a lyophilized powder at room temperature with an activity not less than five units per ampule, stabilized with serum albumen, are commercially available from Seikagayu Kogyo Co., Ltd. of Tokyo, Japan. These enzymes are not suitable for pharmaceutical applications in the present commercial form in which they are sold. One unit of enzyme will mediate the release of one micromole of 4.5 unsaturated disaccharide from a substrate of chondroitinase sulfates AB and C per minute at 37° C., pH 6.0. One unit of enzyme is that quantity of enzyme which converts chondroitinase sulfate A and C to 4.5 unsaturated disaccharides. One unit of enzyme will release 1 micromole of product per minute at 37° C., 6.0 pH.

Highly purified Chondroitinase ABC, as a freeze-dried powder with an activity of five units per ampule, is also available as a commercial product.

The chondroitinase for pharmaceutical applications differs from the commercial product presently sold in that the purified enzyme (ABC or AC) is freeze dried, in a sterile form, without preservatives, and maintained at −20° C. until just prior to use. The inventor has defined these parameters, of enzyme suitable for pharmaceutical applications, and has secured them according to his specifications as here defined, from the Seikagaya Kogyo Co.

The enzymes are used in one dose vials containing 100 units of lyophilized, sterile, pyrogen-free, purified enzyme powder, refrigerated at −20° C. and stored at −20° C. until immediately prior to use. The vial should be allowed to warm to room temperature and be immediately reconstituted in 2cc of sterile water without preservatives. Administration should be made into the center of the disc by the standard technique of intradiscal injection as described in the inventor's book, *Intradiscal Therapy*, Year Book Medical Publishers, Inc., Chicago, 1983.

The following Examples are presented for purposes of illustrating the invention:

EXAMPLE I

A forty-five-year-old male complains of right leg pain over a three-month period. He has a ten-year history of intermittent back pain which seems to clear up when the leg pain begins. He has no relief despite two weeks of hospitalization with bedrest and traction. He is medically examined and screened for contraindications to chemonucleolysis. A myelogram demonstrates a large extradural defect lateral at the fifth lumber interspace consistent with disc displacement. Chemonucleolysis with Chondroitinase ABC, or AC, in the form of 50 units per cc sterile water without preservatives, total 2cc volume, is performed at the fifth lumbar disc level. Ten minutes after the injection, the patient has relief of right leg pain. He is observed for two days in the hospital and walks easily without leg pain. He does not require medication. The patient returns to work three weeks after injection. A routine follow-up shows the patient has an excellent result, with complete relief of right leg pain.

EXAMPLE II

A thirty-seven -year-old female develops severe recurrent low back pain and bilateral leg pain, the left side being worse than the right three years following a successful chymopapain treatment at the L5S1 level. The back pain begins after strenuous sport activity two months prior to clinic admission. One month before admission, the patient develops severe left leg pain and has some relief from the back pain. She is medically examined and screened for contraindications to chemonucleolysis. A myelogram demonstrates a large central disc displacement between the fourth and fifth lumbar interspace. Two cc of fluid containing 100 units of Chondroitinase AC or ABC, is injected into the fourth lumbar disc. The patient is discharged two days later walking comfortably. She does not require any narcotic medication during the observation period. The patient returns to work two weeks following the injection and to full recreational activity three months after injection. One year later, she remains fully active at work and recreational activities. She does not require any further treatment. The availability of antigenically different enzymes for chemonucleolysis benefits this patient since reinjection with the same enzyme is contraindicated where prior sensitization may result in a serious systemic reaction.

EXAMPLE III

A fifty-year-old male has a lengthy history of sciatic pain. Previously treated by discolysis with collagenase the pain becomes worse. At follow-up examinations, he constistently complains of leg pain when walking. A repeat CAT scan confirms the diagnosis of peristent disc displacement at L-4 on the left. He undergoes chemonucleosis at the fourth lumbar interspace with chondroitinase AC or ABC. He has immediate partial pain relief in the left leg which improves over the ensuing weeks. He returns to work within four days after the injection. Three months after injection, his excellent results continue.

The mechanism in collagenase dissolves the structural collagen protein which allows expansion of the remaining cartilage to cause pain and nerve deficits. The addition of chondroitinase would prevent the expansion of the residual cartilage because it breaks down the polysaccharide of the cartilage.

The availability of an enzyme(s) with a different substrate activity (polysaccharide vs. collagen) has advantages in the treatment of those who fail or would fail to respond to collagenase.

In view of the preceding description, further modifications and alternative embodiments of the instant invention will be apparent to those skilled in the art. Accordingly, the preceding description and examples are to be construed as explanatory and illustrative only and are for the purpose of teaching and enabling those skilled in the art to practice this invention. It should be understood that the amount of the pharmacologically suitable solution of enzymes required for the dissolution of mammalian disc tissue will vary.

The enzyme's pharmaceutical use is not limited to nucleus pulposus, but should find application in the treatment of ganglia, arthroscopy of joints, certain eye conditions, tumors, and other unwanted cartilage tissue.

While the preferred embodiment of the above described invention is to be understood to be the best mode presently contemplated, it is by no means the only embodiment possible. The scope of the invention is defined by the following claims and by any equivalent modifications and variations that may fall within the true spirit of the invention.

What is claimed is:

1. A method for the treatment of intervertebral disc displacement in humans who have been medically examined and screened for contraindications to chemonucleolysis which comprises administering an effective amount of the cartilage-dissolving enzyme chondroitenase directly into the intervertebral disc space.

2. The method of claim 1 wherein the concentration of chondroitenase constituting the effective amount is 100 units per human disc in the form of 50 units per cc of sterile water without preservatives.

3. A method for the treatment of intervertebral disc displacement in humans who have been medically examined and screened for contraindications to chemonucleolysis which comprises administering an effective amount of the cartilage-dissolving enzyme chondroitenase directly into the intervertebral disc space, said chondroitenase being produced from the bacteria Proteus vulgaris.

4. A method for the treatment of intevertebral disc displacement in humans who have been medically examined and screened for contraindications to chemonucleolysis which comprises administering an effective amount of the cartilage-dissolving enzyme chondroitenase directly into the intervertebral disc space, said chondroitenase being produced from the bacteria Arthrobacter auerescens.

5. A pharmaceutical composition comprising a sterile solution containing as an active ingredient chondroitenase in an admixture with sterile water without preservatives, said solution being adapted to be injected into a patient for the treatment of intervertebral disc displacement.

* * * * *